United States Patent
Kai et al.

(10) Patent No.: US 10,492,495 B2
(45) Date of Patent: Dec. 3, 2019

(54) AGROCHEMICAL COMPOSITION

(71) Applicant: Nippon Soda Co., Ltd., Chiyoda-ku, Tokyo (JP)

(72) Inventors: Tetsutaro Kai, Makinohara (JP); Eriko Okada, Makinohara (JP); Takahiro Maekawa, Makinohara (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 15/550,120

(22) PCT Filed: Feb. 12, 2016

(86) PCT No.: PCT/JP2016/054085
§ 371 (c)(1),
(2) Date: Aug. 10, 2017

(87) PCT Pub. No.: WO2016/133011
PCT Pub. Date: Aug. 25, 2016

(65) Prior Publication Data
US 2018/0014543 A1     Jan. 18, 2018

(30) Foreign Application Priority Data
Feb. 17, 2015   (JP) ................... 2015-028628

(51) Int. Cl.
| | |
|---|---|
| A01N 43/90 | (2006.01) |
| A01N 25/04 | (2006.01) |
| A01N 25/22 | (2006.01) |
| A01N 25/02 | (2006.01) |

(52) U.S. Cl.
CPC ............ *A01N 43/90* (2013.01); *A01N 25/02* (2013.01); *A01N 25/04* (2013.01); *A01N 25/22* (2013.01)

(58) Field of Classification Search
CPC ........ A01N 43/90; A01N 25/02; A01N 25/04; A01N 25/22
See application file for complete search history.

(56) References Cited

U.S. PATENT DOCUMENTS

| | | | |
|---|---|---|---|
| 5,230,893 A | 7/1993 | Gotou et al. | |
| 2001/0029240 A1 | 10/2001 | Hasebe et al. | |
| 2008/0153704 A1 | 1/2008 | Yamaji et al. | |
| 2009/0312387 A1 | 12/2009 | Sirinyan et al. | |
| 2010/0041694 A1 | 2/2010 | Takaishi et al. | |
| 2012/0289700 A1* | 11/2012 | Hamamoto | A01N 43/40 544/238 |
| 2012/0309964 A1* | 12/2012 | Hamamoto | A01N 43/42 544/47 |

FOREIGN PATENT DOCUMENTS

| | | | |
|---|---|---|---|
| CN | 101879163 A | * | 11/2010 |
| CN | 102550573 A | * | 7/2012 |
| JP | 2009-108021 A | | 5/2009 |
| KR | 102009010034 A | | 9/2009 |
| TW | 201127294 A1 | | 8/2011 |
| TW | 201139439 A1 | | 11/2011 |
| WO | WO 2008/080541 A1 | | 7/2008 |
| WO | WO 2010/129345 A2 | | 11/2010 |
| WO | WO 2011/078081 A1 | | 6/2011 |
| WO | WO 2011/105506 A1 | | 9/2011 |

OTHER PUBLICATIONS

International Search Report dated May 10, 2016, in PCT/JP2016/054085.
Supplementary European Search Report dated Jun. 25, 2018, in EP 16752397.6.
KR Notice of Allowance issued in Appl. Ser. No. 10-2017-7022443, dated Feb. 26, 2019, 3 pages.
Office Action dated Oct. 1, 2018, in Colombian Application No. NC2017/0008072, with partial English translation.
Office Action dated Aug. 22, 2019, in Colombian Application No. NC2017/0008072, with English translation.

* cited by examiner

*Primary Examiner* — Timothy P Thomas
*Assistant Examiner* — George W Kosturko
(74) *Attorney, Agent, or Firm* — Foley & Lardner LLP

(57) ABSTRACT

An agrochemical composition contains a component (A): a compound represented by formula (I) (wherein, $R_1$, $R_2$, $R_{3a}$, $R_{3b}$, $R_{4a}$, $R_{4b}$, and $R_5$ each independently represents an unsubstituted or substituted C1-6 alkyl group or the like, n represents an integer of 0 to 4, o and p each independently represents an integer of 2 to 4, and X represents a carbon atom or a nitrogen atom) or a salt thereof, and a component (B): a hydrolysis inhibitor.

(I)

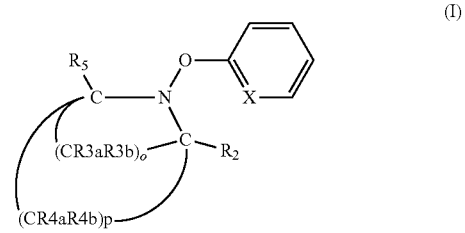

14 Claims, No Drawings

AGROCHEMICAL COMPOSITION

TECHNICAL FIELD

The present invention relates to an agrochemical composition. The present invention more particularly relates to an agrochemical composition containing a compound having an azabicyclo structure, the residual activity thereof being improved.

The present invention is the U.S. National Stage of PCT/JP2016/054085, filed Feb. 12, 2016, which claims priority on the basis of Japanese Patent Application No. 2015-028628 filed in Japan on Feb. 17, 2015, the contents of which are incorporated herein by reference.

BACKGROUND OF THE INVENTION

Patent Document 1 or 2 discloses cyclic amine compounds such as a compound having an azabicyclo structure. These compounds exhibit control effects on mites harmful to crops.

In addition, some of these compounds are decomposed due to organic acids such as sodium ascorbate or DL-malic acid or light. If there is decomposability against sodium ascorbate, the possibility of being decomposed on plants is high because sodium ascorbate is present on plants. If there is decomposability against light, the possibility of being decomposed on plants under sunshine is high. These decompositions increase the necessary amount of agricultural chemical ingredients, and thereby a method of suppressing such decomposition has been awaited.

DOCUMENTS OF RELATED ART

Patent Documents

Patent Document 1 WO 2011/078081 A1
Patent Document 2 WO 2011/105506 A1

SUMMARY OF THE INVENTION

Problems to be Solved by the Invention

The durability of acaricidal effects of an acaricide containing a compound having an aryloxyazabicylo structure is not sufficient due to decomposition of the compound having an aryloxyazabicylo structure by light or sodium ascorbate on plants when the acaricide is sprayed on plants and then applied with sunlight, or due to flowing out by rain or the like.

An object of the present invention is to provide an agrochemical composition containing a compound having an aryloxyazabicyclo structure, the residual activity thereof being improved.

Means to Solve the Problems

The present invention includes the following aspects.
(1) An agrochemical composition containing:
a component (A): a compound represented by formula (I) or a salt thereof; and
a component (B): a hydrolysis inhibitor.

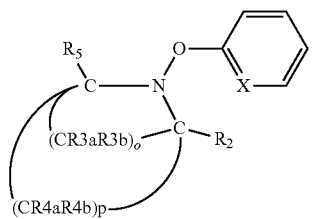

In the formula,
$R_1$, $R_2$, $R_{3a}$, $R_{3b}$, $R_{4a}$, $R_{4b}$, and $R_5$ each independently represent a hydrogen atom, an unsubstituted or substituted C1-6 alkyl group, an unsubstituted or substituted C3-8 cycloalkyl group, an unsubstituted or substituted C2-6 alkenyl group, an unsubstituted or substituted C2-6 alkynyl group, a hydroxyl group, an unsubstituted or substituted C1-6 alkoxy group, an unsubstituted or substituted C3-8 cycloalkoxy group, an unsubstituted or substituted C2-6 alkenyloxy group, an unsubstituted or substituted C2-6 alkynyloxy group, a carboxyl group, an unsubstituted or substituted C1-7 acyl group, an unsubstituted or substituted C1-6 alkoxycarbonyl group, an unsubstituted or substituted C3-8 cycloalkyloxycarbonyl group, an unsubstituted or substituted C2-6 alkenyloxycarbonyl group, an unsubstituted or substituted C2-6 alkynyloxycarbonyl group, an unsubstituted or substituted C6-10 aryloxycarbonyl group, an unsubstituted or substituted heterocyclyloxycarbonyl group, an unsubstituted or substituted C1-7 acyloxy group, an unsubstituted or substituted C1-6 alkoxycarbonyloxy group, an unsubstituted or substituted C3-8 cycloalkyloxycarbonyloxy group, an unsubstituted or substituted C2-6 alkenyloxycarbonyloxy group, an unsubstituted or substituted C2-6 alkynyloxycarbonyloxy group, an unsubstituted or substituted C1-6 alkylaminocarbonyloxy group, an unsubstituted or substituted C3-8 cycloalkylaminocarbonyloxy group, an unsubstituted or substituted C2-6 alkenylaminocarbonyloxy group, an unsubstituted or substituted C2-6 alkynylaminocarbonyloxy group, an unsubstituted or substituted C6-10 arylaminocarbonyloxy group, an unsubstituted or substituted heterocyclylaminocarbonyloxy group, an unsubstituted or substituted C1-6 alkylideneaminooxy group, an unsubstituted or substituted C6-10 aryl group, an unsubstituted or substituted heterocyclyl group, an unsubstituted or substituted C6-10 aryloxy group, an unsubstituted or substituted heterocyclyloxy group, a substituted sulfonyloxy group, an unsubstituted or substituted aminocarbonyl group, a cyano group, a nitro group, or a halogeno group,
n represents a number of $R_1$ and is an integer of 0 to 4,
o represents a number of $(CR_{3a}R_{3b})$ and is an integer of 2 to 4,
p represents a number of $(CR_{4a}R_{4b})$ and is an integer of 2 to 4, and
X represents a carbon atom or a nitrogen atom.
(2) The agrochemical composition according to (1), wherein the component (B) is a compound represented by formula (II).

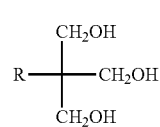

In the formula, R represents a hydrogen atom, a C1-4 alkyl group, a C2-4 alkenyl group, or a C2-4 alkynyl group.

(3) The agrochemical composition according to (1), wherein the component (B) is at least one selected from the group consisting of an oxalic acid, a gallic acid, a tartaric acid, a starch, a cellulose, a sorbitol, a polyglycerin, a polyvinyl alcohol, a glucose, and a citric acid.

(4) The agrochemical composition according to (1), wherein the component (B) is a component (C): a polycarboxylic acid or a salt thereof.

(5) The agrochemical composition according to (2) or (3), further containing a component (C): a polycarboxylic acid or a salt thereof.

(6) The agrochemical composition according to (2) or (3), wherein, relative to a total mass of the agrochemical composition, an amount of the component (A) is 1 to 50% by mass, an amount of the component (B) is 1 to 40% by mass, and a mass ratio of the component (A)/the component (B) is 20/1 to 1/20.

(7) The agrochemical composition according to any one of (1) to (6), wherein the agrochemical composition is in an aqueous suspension state.

Effects of the Invention

The agrochemical composition according to the present invention exhibits a high residual ratio of a compound having an azabicyclo structure that is an agricultural active ingredient after being sprayed. The use of the agrochemical composition according to the present invention makes it possible to control mites harmful to agricultural crops by exhibiting acaricidal effects over a long-term period.

EMBODIMENTS FOR CARRYING OUT THE INVENTION

An agrochemical composition according to the present invention contains a component (A) and a component (B).

(Component (A))

A component (A) available in the present invention is a compound represented by formula (I) (hereinafter, abbreviated as compound (I)) or a salt of the compound (I).

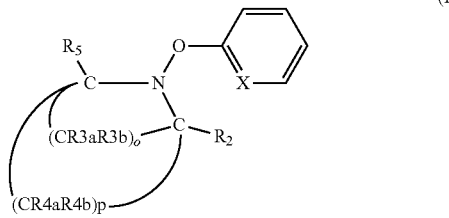

(I)

In the formula (I), $R_1$, $R_2$, $R_{3a}$, $R_{3b}$, $R_{4a}$, $R_{4b}$, and $R_5$ each independently represent a hydrogen atom, an unsubstituted or substituted C1-6 alkyl group, an unsubstituted or substituted C3-8 cycloalkyl group, an unsubstituted or substituted C2-6 alkenyl group, an unsubstituted or substituted C2-6 alkynyl group, a hydroxyl group, an unsubstituted or substituted C1-6 alkoxy group, an unsubstituted or substituted C3-8 cycloalkoxy group, an unsubstituted or substituted C2-6 alkenyloxy group, an unsubstituted or substituted C2-6 alkynyloxy group, a carboxyl group, an unsubstituted or substituted C1-7 acyl group, an unsubstituted or substituted C1-6 alkoxycarbonyl group, an unsubstituted or substituted C3-8 cycloalkyloxycarbonyl group, an unsubstituted or substituted C2-6 alkenyloxycarbonyl group, an unsubstituted or substituted C2-6 alkynyloxycarbonyl group, an unsubstituted or substituted C6-10 aryloxycarbonyl group, an unsubstituted or substituted heterocyclyloxycarbonyl group, an unsubstituted or substituted C1-7 acyloxy group, an unsubstituted or substituted C1-6 alkoxycarbonyloxy group, an unsubstituted or substituted C3-8 cycloalkyloxycarbonyloxy group, an unsubstituted or substituted C2-6 alkenyloxycarbonyloxy group, an unsubstituted or substituted C2-6 alkynyloxycarbonyloxy group, an unsubstituted or substituted C1-6 alkylaminocarbonyloxy group, an unsubstituted or substituted C3-8 cycloalkylaminocarbonyloxy group, an unsubstituted or substituted C2-6 alkenylaminocarbonyloxy group, an unsubstituted or substituted C2-6 alkynylaminocarbonyloxy group, an unsubstituted or substituted C6-10 arylaminocarbonyloxy group, an unsubstituted or substituted heterocyclylaminocarbonyloxy group, an unsubstituted or substituted C1-6 alkylideneaminooxy group, an unsubstituted or substituted C6-10 aryl group, an unsubstituted or substituted heterocyclyl group, an unsubstituted or substituted C6-10 aryloxy group, an unsubstituted or substituted heterocyclyloxy group, a substituted sulfonyloxy group, an unsubstituted or substituted aminocarbonyl group, a cyano group, a nitro group, or a halogeno group, n represents a number of $R_1$ and is an integer of 0 to 4, o represents a number of ($CR_{3a}R_{3b}$) and is an integer of 2 to 4, p represents a number of ($CR_{4a}R_{4b}$) and is an integer of 2 to 4, and X represents a carbon atom or a nitrogen atom.

First, the meanings of the terms "unsubstituted" and "substituted" in the formula (I) will be explained.

The term "unsubstituted" means that the specified group is solely formed of a group serving as a mother nucleus. When only the name of the group serving as the mother nucleus is mentioned without mention of "substituted", it means "unsubstituted" unless otherwise stated.

On the other hand, the term "substituted" means that a hydrogen atom of a group serving as a mother nucleus has been substituted with a substituent having the same structure as or a different structure from the mother nucleus. The "substituent" is a different group which is bonded to the group serving as a mother nucleus. The "substituent" may be one or two or more. At least two substituents may be the same or different. For example, a substituted C1-6 alkyl group has an alkyl group having 1 to 6 carbon atoms as a mother nucleus, any of hydrogen atoms of the alkyl group being substituted with (a) group(s) having a structure different therefrom.

Terms such as "C1-6" or the like indicate that the number of carbon atoms in a group serving as a mother nucleus is 1 to 6 or the like. The number of carbon atoms does not include the number of carbon atoms in a substituent. For example, a butyl group having an epoxy group as a substituent is categorized as a C2 alkoxy C4 alkyl group.

The "substituent" is not particularly limited as long as it is chemically acceptable and has effects of the present invention.

Possible examples of the "substituent" include: a halogeno group such as a fluoro group, a chloro group, a bromo group, or an iodo group;

an alkyl group such as a methyl group, an ethyl group, a n-propyl group, an i-propyl group, a n-butyl group, a s-butyl group, an i-butyl group, a t-butyl group, a n-pentyl group, or a n-hexyl group, preferably a C1-6 alkyl group;

a cycloalkyl group such as a cyclopropyl group, a cyclobutyl group, a cyclopentyl group, a cyclohexyl group, or a cycloheptyl group, preferably a C3-8 cycloalkyl group;

an alkenyl group such as a vinyl group, a 1-propenyl group, a 2-propenyl group, a 1-butenyl group, a 2-butenyl group, a 3-butenyl group, a 1-methyl-2-propenyl group, a 2-methyl-2-propenyl group, a 1-pentenyl group, a 2-pentenyl group, a 3-pentenyl group, a 4-pentenyl group, a 1-methyl-2-butenyl group, a 2-methyl-2-butenyl group, a 1-hexenyl group, a 2-hexenyl group, a 3-hexenyl group, a 4-hexenyl group, a 5-hexenyl group, and a cinnamyl group, preferably a C2-6 alkyenyl group;

a cycloalkenyl group such as a 2-cyclopropenyl group, a 2-cyclopentenyl group, a 3-cyclohexenyl group, or a 4-cyclooctenyl group, preferably a C3-8 cycloalkenyl group;

an alkynyl group such as an ethynyl group, a 1-propynyl group, a 2-propynyl group, a 1-butynyl group, a 2-butynyl group, a 3-butynyl group, a 1-methyl-2-propynyl group, a 2-methyl-3-butynyl group, a 1-pentynyl group, a 2-pentynyl group, a 3-pentynyl group, a 4-pentynyl group, a 1-methyl-2-butynyl group, a 2-methyl-3-pentynyl group, a 1-hexynyl group, or a 1,1-dimethyl-2-butynyl group, preferably a C2-6 alkynyl group;

an alkoxy group such as a methoxy group, an ethoxy group, a n-propoxy group, an i-propoxy group, a n-butoxy group, a s-butoxy group, an i-butoxy group, or a t-butoxy group, preferably a C1-6 alkoxy group;

an alkenyloxy group such as a vinyloxy group, an allyloxy group, a propenyloxy group, or a butenyloxy group, preferably a C2-6 alkenyloxy group;

an alkynyloxy group such as an ethynyloxy group or a propargyloxy group, preferably a C2-6 alkynyloxy group;

an aryl group such as a phenyl group, a 1-naphthyl group, or a 2-naphthyl group, preferably a C6-10 aryl group;

an aryloxy group such as a phenoxy group or a 1-naphthoxy group, preferably a C6-10 aryloxy group;

an aralkyl group such as a benzyl group or a phenethyl group, preferably a C7-11 aralkyl group;

an aralkyloxy group such as a benzyloxy group or a phenethyloxy group, preferably a C7-12 aralkyloxy group;

an acyl group such as a formyl group, an acetyl group, a propionyl group, a benzoyl group, or a cyclohexylcarbonyl group, preferably a C1-7 acyl group;

an acyloxy group such as formyloxy group, an acetyloxy group, a propionyloxy group, a benzoyloxy group, or a cyclohexylcarbonyloxy group, preferably a C1-7 acyloxy group;

an alkoxycarbonyl group such as a methoxycarbonyl group, an ethoxycarbonyl group, an n-propoxycarbonyl group, an i-propoxycarbonyl group, an n-butoxycarbonyl group, and a t-butoxycarbonyl group, preferably a C1-6 alkoxycarbonyl group;

a carboxyl group;

a hydroxyl group;

a haloalkyl group such as a chloromethyl group, a chloroethyl group, a 1,2-dichloro-n-propyl group, a 1-fluoro-n-butyl group, or a perfluoro-n-pentyl group, preferably a halo C1-6 alkyl group;

a haloalkenyl group such as a 2-chloro-1-propenyl group or a 2-fluoro-1-butenyl group, preferably a halo C2-6 alkenyl group;

a haloalkynyl group such as a 4,4-dichloro-1-butynyl group, a 4-fluoro-1-pentynyl group or a 5-bromo-2-pentynyl group, preferably a halo C2-6 alkynyl group;

a haloalkoxy group such as a 2-chloro-n-propoxy group or a 2,3-dichlorobutoxy group, preferably a halo C1-6 alkoxy group;

a haloalkenyloxy group such as a 2-chloropropenyloxy group or a 3-bromobutenyloxy group, preferably a halo C2-6 alkenyloxy group;

a haloaryl group such as a 4-chlorophenyl group, a 4-fluorophenyl group, or a 2,4-dichlorophenyl group, preferably a halo C6-10 aryl group;

a haloaryloxy group such as a 4-fluorophenyloxy group, or a 4-chloro-1-naphthoxy group, preferably a halo C6-10 aryloxy group;

a haloacyl group such as a chloroacetyl group, a trifluoroacetyl group, a trichloroacetyl group, or a 4-chlorobenzoyl group;

a cyano group; an isocyano group; a nitro group; an isocyanato group; a cyanato group; an amino group;

an alkylamino group such as a methylamino group, a dimethylamino group, or a diethylamino group;

an arylamino group such as an anilino group, a naphthylamino group, or an anthracenylamino group;

an aralkylamino group such as a benzylamino group or a phenylethylamino group;

an alkylsulfonylamino group such as a methylsulfonylamino group, an ethylsulfonylamino group, a n-propylsulfonylamino group, an i-propylsulfonylamino group, a n-butylsulfonylamino group, or a t-butylsulfonylamino group, preferably a C1-6 alkylsulfonylamino group;

an arylsulfonylamino group such as a phenylsulfonylamino group, preferably a C6-10 arylsulfonylamino group;

a heterocyclic sulfonylamino group such as a piperazinyl sulfonylamino group, preferably a 3- to 6-membered heterocyclic sulfonylamino group;

an acylamino group such as a formylamino group, an acetylamino group, a propanoylamino group, a butyrylamino group, an i-propylcarbonylamino group, or a benzoylamino group, preferably a C1-7acylamino group;

an alkoxycarbonylamino group such as a methoxycarbonylamino group, an ethoxycarbonylamino group, a n-propoxcarbonylamino group, or an i-propoxcarbonylamino group, preferably a C1-6 alkoxycarbonylamino group;

a haloalkylsulfonylamino group such as a fluoro methylsulfonylamino group, a chloromethylsulfonylamino group, a bromo methylsulfonylamino group, a difluoromethylsulfonylamino group, a dichloromethylsulfonylamino group, a 1,1-difluoroethylsulfonylamino group, a trifluoromethylsulfonylamino group, a 1,1,1-trifluoroethylsulfonylamino group, or a pentafluoroethylsulfonylamino group, preferably a halo C1-6 alkylsulfonylamino group;

a bis(alkylsulfonyl) amino group such as a bis(methylsulfonyl) amino group, a bis(ethylsulfonyl) amino group, an (ethylsulfonyl) (methylsulfonyl) amino group, a bis(n-propylsulfonyl) amino group, a bis(i-propylsulfonyl) amino group, a bis(n-butylsulfonyl) amino group, or a bis(t-butylsulfonyl) amino group, preferably a bis(C1-6 alkylsulfonyl) amino group;

a bis(haloalkylsulfonyl) amino group such as a bis(fluoromethylsulfonyl) amino group, a bis(chloromethylsulfonyl) amino group, a bis(bromomethylsulfonyl) amino group, a bis(difluoromethylsulfonyl) amino group, a bis(dichloromethylsulfonyl) amino group, a bis(1,1-difluoroethylsulfonyl) amino group, a bis(trifluoromethylsulfonyl) amino group, a bis(1,1,1-trifluoroethylsulfonyl) amino group, or a bis(pentafluoroethylsulfonyl) amino group, preferably a bis(halo C1-6 alkylsulfonyl) amino group;

an unsubstituted or substituted hydrazino group such as a hydrazino group, a N'-phenylhydrazino group, a N'-methoxycarbonylhydrazino group, a N'-acetylhydrazino group, or a N'-methylhydrazino group;

an unsubstituted or substituted aminocarbonyl group such as an aminocarbonyl group, a dimethylaminocarbonyl group, a phenylaminocarbonyl group, or a N-phenyl-N-methylaminocarbonyl group;

an unsubstituted or substituted hydrazinocarbonyl group such as a hydrazinocarbonyl group, a N'-methylhydrazinocarbonyl group, or a N'-phenylhydrazinocarbonyl group;

a N-unsubstituted or N-substituted iminoalkyl group such as a N-methyliminomethyl group, a 1-N-phenyliminoethyl group, a N-hydroxyiminomethyl group, or a N-methoxyiminomethyl group;

a mercapto group; an isothiocyano group; a thiocyano group;

an alkylthio group such as a methylthio group, an ethylthio group, a n-propylthio group, an i-propylthio group, a n-butylthio group, an i-butylthio group, a s-butylthio group, or a t-butylthio group, preferably a C1-6 alkylthio group;

an alkenylthio group such as a vinylthio group or an allylthio group, preferably a C2-6 alkenylthio group;

an alkynylthio group such as an ethynylthio group or a propargylthio group, preferably a C2-6 alkynylthio group;

an arylthio group such as a phenylthio group or a naphthylthio group, preferably a C6-10 arylthio group;

a heteroarylthio group such as a 2-pyridylthio group or a 3-pyridazylthio group, preferably a 5- to 6-membered heteroarylthio group;

an aralkylthio group such as a benzylthio group or a phenethylthio group, preferably a C7-10 aralkylthio group;

an alkylthiocarbonyl group such as a methylthiocarbonyl group, an ethylthiocarbonyl group, a n-propylthiocarbonyl group, an i-propylthiocarbonyl group, a n-butylthiocarbonyl group, an i-butylthiocarbonyl group, a s-butylthiocarbonyl group, or a t-butylthiocarbonyl group, preferably a C1-6 alkylthiocarbonyl group;

an alkylsulfinyl group such as a methylsulfinyl group, an ethylsulfinyl group, or a t-butylsulfinyl group, preferably a C1-6 alkylsulfinyl group;

an alkenylsulfinyl group such as an allylsulfinyl group, preferably a C2-6 alkenylsulfinyl group;

an alkynylsulfinyl group such as a propargylsulfinyl group, preferably a C2-6 alkynylsulfinyl group;

an arylsulfinyl group such as a phenylsulfinyl group, preferably a C6-10 arylsulfinyl group;

a heteroarylsulfinyl group such as a 2-pyridylsulfinyl group or a 3-pyridylsulfinyl group, preferably a 5- to 6-membered heteroarylsulfinyl group;

an aralkylsulfinyl group such as a benzylsulfinyl group or a phenethylsulfinyl group, preferably a C7-10 aralkylsulfinyl group;

an alkylsulfonyl group such as a methylsulfonyl group, an ethylsulfonyl group, or a t-butylsulfonyl group, preferably a C1-6 alkylsulfonyl group;

an alkenylsulfonyl group such as an allylsulfonyl group, preferably a C2-6 alkenylsulfonyl group;

an alkynylsulfonyl group such as a propargylsulfonyl group, preferably a C2-6 alkynylsulfonyl group;

an arylsulfonyl group such as a phenylsulfonyl group, preferably a C6-10 arylsulfonyl group;

a heteroarylsulfonyl group such as a 2-pyridylsulfonyl group or a 3-pyridylsulfonyl group, preferably a 5- to 6-membered heteroarylsulfonyl group;

an aralkylsulfonyl group such as a benzylsulfonyl group or a phenethylsulfonyl group, preferably a C7-10 aralkylsulfonyl group;

an unsaturated 5-membered heterocyclic group such as a furan-2-yl group, a furan-3-yl group, a thiophen-2-yl group, a thiophen-3-yl group, a pyrrol-2-yl group, a pyrrol-3-yl group, an oxazol-2-yl group, an oxazol-4-yl group, an oxazol-5-yl group, a thiazol-2-yl group, a thiazol-4-yl group, a thiazol-5-yl group, an isooxazol-3-yl group, an isooxazol-4-yl group, an isooxazol-5-yl group, an isothiazol-3-yl group, an isothiazol-4-yl group, an isothiazol-5-yl group, an imidazol-2-yl group, an imidazol-4-yl group, an imidazol-5-yl group, a pyrazol-3-yl group, a pyrazol-4-yl group, a pyrazol-5-yl group, a 1,3,4-oxaziazol-2-yl group, a 1,3,4-thiadiazol-2-yl group, a 1,2,3-triazol-4-yl group, a 1,2,4-triazol-3-yl group, or a 1,2,4-triazol-5-yl group;

an unsaturated 6-membered heterocyclic group such as a pyridin-2-yl group, a pyridin-3-yl group, a pyridin-4-yl group, a 5-chloro-pyridin-3-yl group, a 3-trifluoromethyl-pyridin-2-yl group, a pyridazin-3-yl group, a pyridazin-4-yl group, a pyrazin-2-yl group, a pyrimidin-2-yl group, a pyrimidin-4-yl group, a pyrimidin-5-yl group, a 1,3,5-triazin-2-yl group, or a 1,2,4-triazin-3yl group;

a saturated heterocyclic group such as a tetrahydrofuran-2-yl group, a tetrahydropyran-4-yl group, a piperidin-3-yl group, a pyrrolidin-2-yl group, a morpholino group, a piperidino group, or a N-methylpiperazinyl group; and a heterocycloxy group such as a 2-pyridyloxy group or a 3-oxazolyloxy group.

Additional examples of the "substituent" include a group represented by —Si($R^6$)($R^7$)($R^8$), such as —Si(Me)$_3$, —SiPh$_3$, —Si(cPr)$_3$, or —Si(Me)$_2$(tBu). $R^6$, $R^7$, and $R^8$ in the formula each independently represent a C1-6 alkyl group, a C3-8 cycloalkyl group, or a phenyl group. Specific examples of the C1-6 alkyl group and the C3-8 cycloalkyl group include the same groups as mentioned above. These "substituents" may further have another "substituent".

It is preferable that $R_1$ in the formula (I) be an unsubstituted or substituted C1-6 alkyl group, and more preferably a halo C1-6 alkyl group.

It is preferable that n in the formula (I) be 1.

It is preferable that X in the formula (I) be a nitrogen atom.

It is preferable that $R_{3a}$ and $R_{3b}$ in the formula (I) each independently represent a hydrogen atom or an unsubstituted or substituted C1-6 alkyl group, and more preferably a hydrogen atom.

It is preferable that o in the formula (I) be 3.

It is preferable that $R_{4a}$ and $R_{4b}$ in the formula (I) each independently represent a hydrogen atom or an unsubstituted or substituted C1-6 alkyl group, and more preferably a hydrogen atom.

It is preferable that p in the formula (I) be 3.

It is preferable that $R_5$ in the formula (I) be an unsubstituted or substituted C6-10 aryloxy group, and more preferably a substituted phenoxy group. It is preferable that a substituent thereof be a C1-6 alkyl group, a halo C1-6 alkyl group, and/or a C1-6 alkoxy group.

It is further preferable that the compound (I) be a compound represented by formula (X).

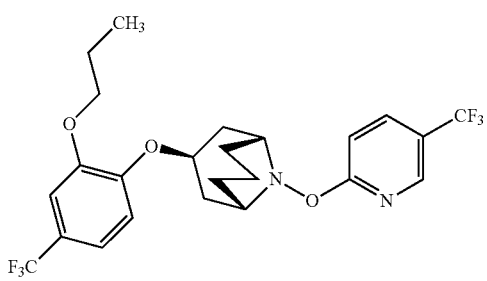

(X)

The compound X is (1R,5R,7S)-7-(2-propoxy-4-(trifluoromethyl) phenoxy)-9-{[5-(trifluoromethyl) pyridin-2-yl]oxy}-9-azabicyclo[3.3.1]non-2-yne.

A salt of the compound (I) is not particularly limited, provided that the salt is an agriculturally and horticulturally acceptable salt. Examples thereof include: salts of an inorganic acid such as a hydrochloric acid or a sulfuric acid; salts of an organic acid such as an acetic acid or a lactic acid; salts of an alkali metal such as a lithium, a sodium, or a potassium; salts of an alkaline earth metal such as a calcium or a magnesium; salts of a transition metal such as an iron or a copper; and salts of an organic base such as an ammonia, a triethylamine, a tributylamine, a pyridine, or a hydrazine.

The compound (I) is not particularly limited by production methods thereof. For example, the compound (I) may be obtained by a method disclosed in Patent Document 1 or 2. In addition, the salt of the compound (I) may be, for example, obtained by a conventional method from the compound (I).

The compound (I) or the salt of the compound (I) has a plant disease controlling activity such as acaricidal activity.

The amount of the component (A) contained in the agrochemical composition according to the present invention, relative to the total mass of the agrochemical composition, is preferably 1 to 50% by mass, more preferably 5 to 30% by mass, and even more preferably 10 o 25% by mass.

(Component (B))

The component (B) available in the present invention is a hydrolysis inhibitor. The hydrolysis inhibitor is a compound that contributes to the suppression of hydrolysis or photolysis of the compound (I) in the presence of a sodium ascorbate that exists on the leaves. Although the hydrolysis inhibitor is not particularly limited, the hydrolysis inhibitor is a compound that increases the amount of the compound (I) 24 hours after the compound (I), an ascorbic acid, and the hydrolysis inhibitor are mixed and then left in a dark place or under the sunshine, in comparison with the case where no hydrolysis inhibitor is added.

The component (B) available in the first aspect of the present invention is a component (B1) that is a compound represented by formula (II) (hereinafter, abbreviated as compound (II)).

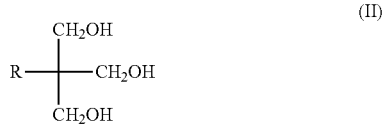

(II)

In the formula (II), R represents a hydrogen atom, a C1-4 alkyl group, a C2-4 alkenyl group, or a C2-4 alkynyl group.

Examples of the C1-4 alkyl group include a methyl group, an ethyl group, a n-propyl group, an i-propyl group, a n-butyl group, a s-butyl group, an i-butyl group, and a t-butyl group.

Examples of the C2-4 alkenyl group include a vinyl group, a 1-propenyl group, a 2-propenyl group, a 1-butenyl group, a 2-butenyl group, a 3-butenyl group, a 1-methyl-2-propenyl group, and a 2-methyl-2-propenyl group.

Examples of the C2-4 alkynyl group include an ethynyl group, a 1-propynyl group, a 2-propynyl group, a 1-butynyl group, a 2-butynyl group, a 3-butynyl group, and a 1-methyl-2-propynyl group.

It is preferable that R in formula (II) be an ethyl group.

Specific examples of the compound (II) include a trimethylolmethane, a trimethylolethane, and a trimethylolpropane.

As the component (B), one kind of the compound (II) may be used alone, or two or more kinds of the compound (II) may be used in combination.

The component (B) available in the second aspect of the present invention is a component (B2) that is at least one selected from the group consisting of an oxalic acid, a gallic acid, a tartaric acid, a starch, a cellulose, a sorbitol, a polyglycerin, a polyvinyl alcohol, a glucose, and a citric acid, and preferably an oxalic acid, a gallic acid, a tartaric acid, a starch, or a cellulose.

As the component (B) available in the present invention, the component (B1) and the component (B2) may be used in combination.

It is preferable that the amount of the component (B) (the total mass of the component B1 and the component B2), relative to the total mass of the agrochemical composition according to the present invention, be 1 to 40% by mass, more preferably 5 to 30% by mass, and even more preferably 10 to 25% by mass.

It is preferable that the mass ratio of the component (A)/the component (B) (the total mass of the component B1 and the component B2) in the agrochemical composition according to the present invention be 1/20 to 20/1, more preferably 1/15 to 15/1, and even more preferably 1/10 to 10/1.

The component (B) available in the third aspect of the present invention is a component (C) that is a polycarboxylic acid or a salt of the polycarboxylic acid.

The polycarboxylic acid is a polymer compound having a carboxylic acid as the main structural unit thereof. The salt of the polycarboxylic acid is a polymer compound having a carboxylic acid salt as the main structural unit thereof. The molecular weight of the polycarboxylic acid or the salt of the polycarboxylic acid is preferably 1,000 to 50,000.

Examples of the polycarboxylic acid include: (1) polymers of ethylenically unsaturated monocarboxylic acids; (2) copolymers of ethylenically unsaturated monocarboxylic acids and ethylenically unsaturated dicarboxylic acids; (3) copolymers of either ethylenically unsaturated monocarboxylic acids or ethylenically unsaturated dicarboxylic acids with alkenes having 2 to 6 carbon atoms, and (4) copolymers of either ethylenically unsaturated monocarboxylic acids or ethylenically unsaturated dicarboxylic acids with aromatic vinyl compounds.

Examples of the ethylenically unsaturated monocarboxylic acid include an acrylic acid, a methacrylic acid, and a crotonic acid.

Examples of the ethylenically unsaturated dicarboxylic acid include a maleic acid, a fumaric acid, and an itaconic acid.

Examples of the alkene having 2 to 6 carbon atoms include an ethylene, a propene, a butylene, an isobutylene, and a diisobutylene.

Examples of the aromatic vinyl compound include a styrene, an α-methylstyrene, a vinyl toluene, and a p-methyl styrene.

Examples of the salt of the polycarboxylic acid include salts in which a hydrogen cation of a carboxyl group in the polycarboxylic acid is substituted with an arbitrary cationic component.

Examples of the cationic component include: alkali metal cations such as a lithium cation, a sodium cation, and a potassium cation; alkaline earth metal cations such as a calcium cation and a magnesium cation; amine cations such as a monomethyl amine cation, a monoethyl amine cation, and a dimethyl amine cation; and an ammonium cation.

Specific examples of the polycarboxylic acid or the salt of the polycarboxylic acid includes an polyacrylic acid, a copolymer of an acrylic acid and a maleic acid, a copolymer of an isobutylene and a maleic anhydride, a copolymer of an acrylic acid and an itaconic acid, a copolymer of a methacrylic acid and an itaconic acid, a copolymer of a maleic acid and a styrene, a copolymer of a maleic acid and a diisobutylene, and salts thereof. Examples of the salts include salts of alkali metal such lithium, sodium, and potassium; salts of alkaline earth metal such as calcium and magnesium; salts of amine such as monomethylamine, monoethylamine, and dimethylamine; and an ammonium salt.

Examples of a salt of a copolymer of an isobutylene and a maleic anhydride include ISOBAM 600SF35 (product name/manufactured by Kuraray Co., Ltd.); examples of a salt of a copolymer of isobutylene and maleic anhydride include Tokisanon GR31A (product name/manufactured by Sanyo Chemical Industries); examples of a polyacrylic acid salt include POISE 530 (product name/manufactured by Kao Corporation); examples of ammonium polyacrylate include POISE 532A (product name/manufactured by Kao Corporation); examples of a salt of a copolymer of acrylic acid and maleic acid include POISE 520 (product name/manufactured by Kao Corporation) and POISE 521 (product name/manufactured by Kao Corporation); examples of a salt of a copolymer of maleic acid and alkene include NEWKALGEN WG-5 (product name/manufactured by TAKEMOTO OIL & FAT Co., Ltd.), S-SMA 3000 (product name/manufactured by ARCO CHEMICAL Company), S-SMA1000 (product name/manufactured by ARCO CHEMICAL Company), S-SMA1440H (product name/manufactured by ARCO CHEMICAL Company), POLYSTAR OMP (product name/manufactured by NOF Corporation), POLYSTAR OMA (product name/manufactured by NOF Corporation), POLYSTAR SMX (product name/manufactured by NOF Corporation), POLYSTAR SM-1015 (product name/manufactured by NOF Corporation), POLYSTAR A-1060 (product name/manufactured by NOF Corporation), SOKALAN CP-5 (product name/manufactured by BASF Corp.), SOKALAN CP-7 (product name/manufactured by BASF Corp.), SOKALAN CP-9 (product name/manufactured by BASF Corp.), SOKALAN CP-10 (product name/manufactured by BASF Corp.), GEROPON T/36 (product name/manufactured by Rhone Poulenc), GEROPON TA/72 (product name/manufactured by Rhone Poulenc), GEROPON SC/213 (product name/manufactured by Rhone Poulenc), and Sorpol-7248 (product name/manufactured by Toho chemical Industry Co., Ltd.).

Among these, an alkali metal salt of a copolymer of a maleic acid and an alkene are particularly preferable as the component (C). Specific examples of the alkali metal salt of a copolymer of a maleic acid and an alkene a maleic acid include a sodium salt of a maleic acid-2,4,4-trimethylpentene copolymer.

As the component (C), one kind of a polycarboxylic acid and polycarboxylic acid salts may be used alone, or at least two thereof may be used in combination. In addition, the component (C) may be used in combination with the component (B1) and/or the component (B2). The residual ratio of the component (A) is further increased by formulating the component (C).

The amount of the component (C) in the agrochemical composition according to the present invention, relative to the total mass of the agrochemical composition, is preferably 1 to 10% by mass, and more preferably 2 to 8% by mass.

The mass ratio of the component (A)/the component (C) in the agrochemical composition according to the present invention is preferably 2/1 to 20/1, and more preferably 3/1 to 10/1.

The agrochemical composition according to the present invention may further contain a cyclic amine compound disclosed in Patent Document 1 or 2 (excepting the component (A): the compound (I) or the salt of the compound (I)).

(Other Components)

The agrochemical composition according to the present invention may further contain an additive generally available in an agricultural and horticultural agent such as a surfactant, a thickener, an antifoam, an antifreeze agent, an organic solvent, a preservative, an antioxidant, a crystallization inhibitor, or a coloring agent. Among these, a surfactant is preferably contained therein.

The amount of the other component, relative to the total mass of the formulation, is 0 to 10% by mass, preferably 0.05 to 5% by mass, and more preferably 0.1 to 4% by mass.

(Other Component: Surfactant)

Examples of a nonionic surfactant include: polyoxyethylene aryl ethers such as polyoxyethylene alkylphenyl ethers, polyoxyethylene benzylphenyl ethers, polyoxyethylene monostyrylphenyl ethers, polyoxyethylene distyrylphenyl ethers, and polyoxyethylene tristyrylphenyl ethers; sucrose fatty acid esters, polyoxyethylene sucrose fatty acid esters, sorbitan fatty acid esters, polyoxyethylene alkylene glycols, and polyoxyethylene.polyoxypropylene block polymers.

Examples of an anionic surfactant include: alkylaryl sulfonates such as sodium alkylaryl sulfonates, calcium alkylaryl sulfonates, and ammonium alkylaryl sulfonates; polyoxyethylene alkylphenyl ether sulfates, polyoxyethylene alkylphenyl ether phosphates, alkyl sulfates, polyoxyethylene alkyl ether sulfates, polyoxyethylene alkyl ether phosphates, dialkyl sulfosuccinates, alkyl naphthalene sulfonate such as sodium alkyl naphthalene sulfonates, formaldehyde polycondensations of naphthalene sulfonates, lignin sulfonates, and polycarboxylates.

Examples of a cationic surfactant include alkyl quaternary ammonium, alkylamine salts, and alkylpyridinium salts.

Examples of an amphoteric surfactant include alkyl betaines, amine oxides, and alkylamino acid salts.

One of these surfactants may be used alone, or two or more thereof may be used in combination.

(Other Component: Thickener)

A thickener is a compound that increases the viscosity, and a polymeric compound is often used. Although HPMC has been already contained in the present composition, an additional thickner excepting the HPMC may be used to further increase the viscosity, unless negative effects such as crystal growth occur.

The thickener is not particularly limited, provided that the thickner is a compound having the above-mentioned property, and one kind thereof or two or more kinds thereof may be used. Examples thereof include a starch, a dextrin, a cellulose, a methyl cellulose, an ethyl cellulose, a carboxymethyl cellulose, a hydroxyethyl cellulose, a hydroxypropyl cellulose, a carboxymethyl starch, a pullulan, a sodium alginate, an ammonium alginate, a propylene glycol alginate, a guar gum, a locust bean gum, a gum arabic, a xanthan gum, a gelatin, a casein, a polyvinyl alcohol, a polyethylene oxide, a polyethylene glycol, an ethylene.propylene block polymer, a sodium polyacrylate, a polyvinyl pyrrolidone, and a carrageenan.

(Other Component: Antifoam)

An antifoam is a compound that suppresses foamimg.

The amount of the antifoam, relative to the total mass of the formulation, is 0 to 5% by mass, preferably 0 to 1% by mass, and more preferably 0.1 to 0.5% by mass.

Examples of the antifoam include SILICONE SM5512 (manufactured by Dow Corning Toray Silicone Co., Ltd.), ANTIFOAM E-20 (manufactured by Kao Corporation), and SILFOAM SE39 (manufactured by Wacker Asahikasei Silicone co., ltd.).

(Other Component: Antifreeze Agent)

An antifreeze agent is a compound that prevents freezing of agrochemical formulations in cold districts.

Examples of the antifreeze agent include an ethylene glycol, a diethylene glycol, a propylene glycol, and glycerin.

(Other Component: Organic Solvent)

An organic solvent is a compound that aids dissolving of an agrochemical active ingredient and is a liquid compound having water solubility.

Examples of an organic solvent include: lower alcohols such as an ethanol and an isopropanol; glycol-based solvents such as an ethylene glycol, a propylene glycol, a dipropylene glycol, a polypropylene glycol, and a glycerin; ketone-based solvents such as an acetone, a methylethyl ketone, and a propylene carbonate; polar solvents such as a dimethylformamide, a dimethyl sulfoxide, an acetonitrile, and a N-methylpyrrolidone.

(Other Component: Preservative)

A preservative is a compound that is used to prevent proliferation of bacteria or fungi.

The amount of the preservative, relative to the total mass of the formulation, is 0 to 5% by mass, preferably 0.01 to 1% by mass, and more preferably 0.02 to 0.5% by mass.

Examples of the preservative include: isothiazoline-based preservatives such as a methylisothiazolinone (MIT, MI), a chloromethylisothiazolinone (CMIT, CMI), an octylisothiazolinone (OIT, OI), a dichlorooctylisothiazolinone (DCOIT, DCOI), and a benzisothiazolinone (BIT): a hexamethylene tetramine, a sodium propionate, a sorbic acid, a sulfurous acid solution, a paraformaldehyde, a benzoic acid, a propyl p-hydroxybenzoate, a methyl p-hydroxybenzoate, a sodium benzoate, an ascorbic acid, an ascorbyl palmitate, and sodium=1,1'-biphenyl-2-olate. Examples of a commercially available preservative include: LEGEND MK (manufactured by Rohm & Haas Company), DENISAIDO BIT-20N (manufactured by Nagase ChemteX Corporation), PROXEL GXL (manufactured by Avecia Co., Ltd.), and CAISSON CG (manufactured by The Dow Chemical Company, Ltd.).

(Other Component: Antioxidant)

An antioxidant is a compound that is used to prevent oxidation of agrochemical formulations.

Examples of the antioxidant include a n-propyl gallate and butylated hydroxyanisole.

(Other Component: Crystallization Inhibitor)

A crystallization inhibitor is a compound that is contained to prevent precipitation of crystals from an agrochemical formulation.

Examples of the crystallization inhibitor include water-soluble resins such as Agrimer VEMA series (manufactured by ISP Co., Ltd.), Agrimer VA series (manufactured by ISP Japana Co., Ltd.), and SOKALAN HP 53 (manufactured by BASF Corp.).

(Other Component: Coloring Agent)

A coloring agent is a compound that is used to color an agrochemical formulation so as to prevent accidental ingestion.

Examples of the coloring agent include: food colorings such as Food Yellow No. 5, Food Red No. 2, and Food Blue No. 2, edible lake dyes, and a ferric oxide.

(Form of Agrochemical Composition)

The form of the agrochemical composition according to the present invention may be a solid or a liquid. It is preferable that the agrochemical composition according to the present invention be in an aqueous suspension state.

The agrochemical composition according to the present invention is not particularly limited by production methods thereof. The agrochemical composition according to the present invention may be prepared by mixing uniformly a part or all of the component (A), the component (B), and the component (C) with water, wet-milling the mixture, and then adding water and the remaining components to the resultant, if necessary, to uniformly mix the mixture.

(Use of Agrochemical Composition)

The agrochemical composition according to the present invention is suitable to be applied on plants (foliar application), soil on which plants grow (soil application), paddy water (application on water surface), or seeds (seed treatment). The agrochemical composition according to the present invention may be diluted with water to a low concentration to be applied. It is preferable that the agrochemical composition be diluted with water such that the concentration of the component (A) is 1 to 10000 ppm and more preferably 10 to 1000 ppm, depending on target crops, diseases, or application methods.

In the case of the foliar application, the agrochemical composition diluted with water as mentioned above is preferably sprayed at 10 to 300 L, more preferably 10 to 100 L, per 10 ares.

In the case of the soli application or the application on a water surface, the agrochemical composition diluted with water as mentioned above is preferably sprayed such that the component (A) is sprayed at 0.1 to 1000 g, more preferably 10 to 100 g per 10 ares.

In the case of the seed treatment, the agrochemical composition diluted with water as mentioned above is preferably sprayed such that the component (A) is sprayed at 0.001 to 50 g per 1 kg of seeds.

Among these application methods, the foliar application on fruit trees is particularly preferable.

(Dosage Form of Agrochemical Composition)

The agrochemical composition according to the present invention may be formulated into a known dosage form. Examples of the dosage form include a flowable agent, an emulsifiable concentrate, a wettable powder, a soluble concentrate, a water-soluble powder, a dustable powder, and a granule. Among these dosage forms, the flowable agent is preferable and a SC (suspension concentrate) agent is more preferable. Formulation may be obtained by known methods.

The general meaning of the flowable agent, the emulsifiable concentrate, the wettable powder, the soluble concentrate, the water-soluble powder, the dustable powder, and the granule will be explained below.

(Flowable Agent (SC Agent (Suspension Concentrate), EW (Emulsion Oil in Water) Agent, or SE (Suspo Emulsiton) Agent))

The flowable agent is a formulation obtained by wet-milling an agrochemical raw material (water-insoluble solid), adding an adjuvant (such as a wetting agent, a dispersing agent, or an antifreeze agent) thereto, and then dispersing the mixture in water, and may be classified into a SC agent, an EW agent, or a SE agent. The EW agent is a formulation in which an agrochemical raw material coated with a water-soluble polymer or an appropriate surfactant is dispersed in water. The SE agent is a formulation including both the SC agent and the EW agent.

(Emulsifiable Concentrate (EC Agent))

The emulsifiable concentrate is a formulation in which an active ingredient having low water solubility and dissolved in an organic solvent is stabilized by the presence of an emulsifier such as a surfactant such that uniform fine particles thereof disperse in water when being stirred in water, and a formulation that becomes cloudy when being diluted with water.

(Wettable Powder (WP Agent))

The wettable powder is a formulation in which fine particles of an active ingredient having low water solubility are mixed with a white carbon or a surfactant, and a formulation that becomes cloudy when being diluted with water.

(Soluble Concentrate (SL Agent))

The soluble concentrate is a liquid formulation containing a water-soluble active ingredient. The soluble concentrate is used directly or after being diluted or dissolved with water. The water dilution is transparent and stable. The term "soluble concentrate" is sometimes used as a general term of an agrochemical to be diluted with water.

(Water-Soluble Powder (SP Agent))

The water-soluble powder is a solid formulation in which a water-soluble active ingredient is in a powder or a granule, and a formulation that easily becomes an aqueous solution when being dissolved in water. The water dilution thereof is transparent and stable.

(Dustable Powder (DP Agent))

The dustable powder is a formulation obtained by diluting an agrochemical raw material with an extender such as a clay, adding a stabilizer or the like to the dilution, as needed, and then pulverizing the resultant to obtain a particular diameter of 44 μm or less and an average particle diameter of approximately 10 μm.

(Granule (GR Agent))

The granule is a granular solid formulation prepared by granulating a mixture of an agrochemical raw material with an extender such as a bentonite or a talc, or by absorbing or coating an agrochemical raw material with a hollow grain (only an extender). The particle size thereof is 300 to 1700 μm.

EXAMPLES

The present invention will be further explained in detail by showing examples below. The present invention is not limited to these examples. The terms "part" and "%" are based on mass.

Raw materials used are shown below.

Compound X: (1R,5R,7S)-7-(2-propoxy-4-(trifluoromethyl)phenoxy)-9-{[5-(trifluoromethyl)pyridin-2-yl]oxy}-9-azabicyclo[3.3.1]non-2-yne 1000-fold dilution of SC liquid containing 20% of Compound X (hereinafter, referred to as "Compound X dilution"):

| | |
|---|---|
| Compound X | 20.2 parts by mass |
| Surfactant | 2.5 parts by mass |
| Polyoxyethylene polyoxypropylene glycol | 0.5 parts by mass |
| Propyleneglycol | 5.0 parts by mass |
| Preservative | 0.3 parts by mass |
| Antifoam | 0.5 parts by mass |
| Thickener | 0.2 parts by mass |
| Carrier | 0.5 parts by mass |
| Water | 970.3 parts by mass |

Example 1

10 mg of an oxalic acid was added to 50 ml of the Compound X dilution, and then dissolved therein to obtain a mixed solution 1.

Comparative Example 1

A comparative mixed solution 1 was obtained in the same manner as in Example 1, except that the amount of the oxalic acid was replaced with 0 mg.

<Stability Test 1>

In a petri dish on which 10 mg of a sodium ascorbate was put so as to simulate the environment on the plant, 2 mL of the mixed solution 1 was put to dissolve the sodium ascorbate. Two sets of the thus obtained sample were prepared. Next, these petri dishes were dried at 40° C. for 6 hours. One set of the two sets was left still for two days in a sunny greenhouse to obtain a sunny greenhouse petri dish 1. The other was left still for two days in a dark place at room temperature to obtain a dark place petri dish 1.

In the same manner, in two sets of petri dishes each on which 10 mg of sodium ascorbate was put, 2 mL of the comparative mixed solution 1 was put on the petri dishes, and then dried at 40° C. for 6 hours. One set of the two sets was left still for two days in a sunny greenhouse to obtain a sunny greenhouse comparative petri dish 1. The other was left still for two days in a dark place at room temperature to obtain a dark place comparative petri dish 1.

After the petri dishes were left still, the amount of the compound X contained in each petri dish was measured by quantitative analysis using HPLC. As a result, the residual ratio of the compound X in the sunny greenhouse petri dish 1 was approximately 7.5 fold of the sunny greenhouse comparative petri dish 1. The residual ratio of the compound X in the dark place petri dish 1 was approximately 5.8 fold of the dark place comparative petri dish 1.

It was confirmed from the comparison of the fact that the residual ratio of the compound X in the dark place comparative petri dish 1 was 12% with the fact that the residual ratio in the absence of an ascorbic acid was approximately 100% that the degradation progressed. In addition, it was confirmed from the comparison of the fact that the residual ratio of the compound X in the sunny greenhouse comparative petri dish 1 was 7% with the fact that the residual ratio in the absence of an ascorbic acid was 93% that the degradation progressed.

It was confirmed from the above results that the presence of the oxalic acid contributed to the suppression of the photolysis and hydrolysis of the compound X.

Note that the residual ratio is a ratio that represents the ratio of the abundance before and after conducting the test, and, for example, the residual ratio of the compound X is the ratio of the abundance of the compound X before and after conducting the test. The residual ratio is shown at a magnification by comparing the residual ratio with another residual ratio, since the abundance before the test is substantially constant, and therefore the magnification substantially indicates a magnification of the compared abundances after the test. For example, the phrase "the residual ratio of the compound X in the sunny greenhouse petri dish 1 was approximately 7. 5 fold of the sunny greenhouse comparative petri dish 1" means that the value obtained by dividing the residual amount of the compound X in the sunny greenhouse petri dish 1 by the residual amount of the compound X in the sunny greenhouse comparative petri dish 1 was approximately 7.5. Hereinafter, the residual ratio and the comparison of the residual ratios are used in the same meaning.

Example 2

A mixed solution 2 was obtained in the same manner as in Example 1, except that a gallic acid was used instead of the oxalic acid in Example 1.
<Stability Test 2>
A sunny greenhouse petri dish 2 and a dark place petri dish 2 were obtained to conduct the stability test in the same manner as in the stability test 1, except that the mixed solution 2 was used instead of the mixed solution 1.

As a result, the residual ratio of the compound X in the sunny greenhouse petri dish 2 was approximately 2.3 fold of the sunny greenhouse comparative petri dish 1. The residual ratio of the compound X in the dark place petri dish 2 was approximately 3.3 fold of the dark place comparative petri dish 1.

It was confirmed from the above results that the presence of the gallic acid contributed to the suppression of the photolysis and the hydrolysis of the compound X.

Example 3

A mixed solution 3 was obtained in the same manner as in Example 1, except that a tartaric acid was used instead of the oxalic acid in Example 1.
<Stability Test 3>
A sunny greenhouse petri dish 3 and a dark place petri dish 3 were obtained to conduct the stability test in the same manner as in the stability test 1, except that the mixed solution 3 was used instead of the mixed solution 1.

As a result, the residual ratio of the compound X in the sunny greenhouse petri dish 3 was approximately 1.8 fold of the sunny greenhouse comparative petri dish 1. In addition, the residual ratio of the compound X in the dark place petri dish 3 was approximately 2.3 fold of the dark place comparative petri dish 1.

It was confirmed from the above-results that the presence of the tartaric acid contributed to the suppression of the photolysis and the hydrolysis of the compound X.

Example 4

A mixed solution 4 was obtained in the same manner as in Example 1, except that a starch was used instead of the oxalic acid in Example 1.

<Stability Test 4>
A sunny greenhouse petri dish 4 and a dark place petri dish 4 were obtained to conduct the stability test in the same manner as in the stability test 1, except that the mixed solution 4 was used instead of the mixed solution 1.

As a result, the residual ratio of the compound X in the sunny greenhouse petri dish 4 was approximately 2.4 fold of the sunny greenhouse comparative petri dish 1. In addition, the residual ratio of the compound X in the dark place petri dish 4 was approximately 2.1 fold of the dark place comparative petri dish 1.

It was confirmed from the above-results that the presence of the starch contributed to the suppression of the photolysis and the hydrolysis of the compound X.

Example 5

A mixed solution 5 was obtained in the same manner as in Example 1, except that a cellulose was used instead of the oxalic acid in Example 1.
<Stability Test 5>
A sunny greenhouse petri dish 5 and a dark place petri dish 5 were obtained to conduct the stability test in the same manner as in the stability test 1, except that the mixed solution 5 was used instead of the mixed solution 1.

As a result, the residual ratio of the compound X in the sunny greenhouse petri dish 5 was approximately 2.0 fold of the sunny greenhouse comparative petri dish 1. In addition, the residual ratio of the compound X in the dark place petri dish 5 was approximately 1.5 fold of the dark place comparative petri dish 1.

It was confirmed from the above-results that the presence of the cellulose contributed to the suppression of the photolysis and the hydrolysis of the compound X.

Example 6

A mixed solution 6 was obtained in the same manner as in Example 1, except that a trimethylolpropane was used instead of the oxalic acid in Example 1.
<Stability Test 6>
A sunny greenhouse petri dish 6 and a dark place petri dish 6 were obtained to conduct the stability test in the same manner as in the stability test 1, except that the mixed solution 6 was used instead of the mixed solution 1.

As a result, the residual ratio of the compound X in the sunny greenhouse petri dish 6 was approximately 1.9 fold of the sunny greenhouse comparative petri dish 1. In addition, the residual ratio of the compound X in the dark place petri dish 6 was approximately 1.4 fold of the dark place comparative petri dish 1.

It was confirmed from the above-results that the presence of the trimethylolpropane contributed to the suppression of the photolysis and hydrolysis of the compound X.

Example 7

A mixed solution 7 was obtained in the same manner as in Example 1, except that a sorbitol was used instead of the oxalic acid in Example 1.
<Stability Test 7>
A dark place petri dish 7 was obtained to conduct the stability test in the same manner as in the stability test 1, except that the mixed solution 7 was used instead of the mixed solution 1.

As a result, the residual ratio of the compound X in the dark place petri dish 7 was approximately 1.6 fold of the dark place comparative petri dish 1.

It was confirmed from the above-results that the presence of the sorbitol contributed to the suppression of the hydrolysis of the compound X.

Example 8

A mixed solution 8 was obtained in the same manner as in Example 1, except that a polyglycerin was used instead of the oxalic acid in Example 1.
<Stability Test 8>
A dark place petri dish 8 was obtained to conduct the stability test in the same manner as in the stability test 1, except that the mixed solution 8 was used instead of the mixed solution 1.

As a result, the residual ratio of the compound X in the dark place petri dish 8 was approximately 2.3 fold of the dark place comparative petri dish 1.

It was confirmed from the above-results that the presence of the polyglycerin contributed to the suppression of the hydrolysis of the compound X.

Example 9

A mixed solution 9 was obtained in the same manner as in Example 1, except that a polyvinyl alcohol was used instead of the oxalic acid in Example 1.
<Stability Test 9>
A dark place petri dish 9 was obtained to conduct the stability test in the same manner as in the stability test 1, except that the mixed solution 9 was used instead of the mixed solution 1.

As a result, the residual ratio of the compound X in the dark place petri dish 9 was approximately 1.3 fold of the dark place comparative petri dish 1.

It was confirmed from the above-results that the presence of the polyvinyl alcohol contributed to the suppression of the hydrolysis of the compound X.

Example 10

A mixed solution 10 was obtained in the same manner as in Example 1, except that a glucose was used instead of the oxalic acid in Example 1.
<Stability Test 10>
A dark place petri dish 10 was obtained to conduct the stability test in the same manner as in the stability test 1, except that the mixed solution 10 was used instead of the mixed solution 1.

As a result, the residual ratio of the compound X in the dark place petri dish 10 was approximately 1.3 fold of the dark place comparative petri dish 1.

It was confirmed from the above-results that the presence of the glucose contributed to the suppression of the hydrolysis of the compound X.

Example 11

A mixed solution 11 was obtained in the same manner as in Example 1, except that a citric acid was used instead of the oxalic acid in Example 1.
<Stability Test 11>
A dark place petri dish 11 was obtained to conduct the stability test in the same manner as in the stability test 1, except that the mixed solution 11 was used instead of the mixed solution 1.

As a result, the residual ratio of the compound X in the dark place petri dish 11 was approximately 1.2 fold of the dark place comparative petri dish 1.

It was confirmed from the above-results that the presence of the citric acid contributed to the suppression of the hydrolysis of the compound X.

Comparative Example 2

A comparative mixed solution 2 was obtained in the same manner as in Example 1, except that glycerin was used instead of the oxalic acid in Example 1.
<Stability Test 12>
The sunny greenhouse comparative petri dish 2 was obtained to conduct the stability test in the same manner as in the stability test 1, except that the comparative mixed solution 2 was used instead of the mixed solution 1.

As a result, the residual ratio of the compound X in the sunny greenhouse comparative petri dish 2 was approximately 0.3 fold of the sunny greenhouse comparative petri dish 1.

It was confirmed from the above-results that the presence of the glycerin contributed to the promotion of the photolysis of the compound X.

Comparative Example 3

A comparative mixed solution 3 was obtained in the same manner as in Example 1, except that an acetic acid was used instead of the oxalic acid in Example 1.
<Stability Test 13>
A sunny greenhouse comparative petri dish 3 and a dark place comparative petri dish 3 were obtained to conduct the stability test in the same manner as in the stability test 1, except that the comparative mixed solution 3 was used instead of the mixed solution 1.

As a result, the residual ratio of the compound X in the sunny greenhouse comparative petri dish 3 was approximately 0.6 fold of the sunny greenhouse comparative petri dish 1. The residual ratio of the compound X in the dark place comparative petri dish 3 was approximately 0.6 fold of the dark place comparative petri dish 1.

It was confirmed from the above-results that the presence of the acetic acid contributed to the promotion of the photolysis and hydrolysis of the compound X.

Comparative Example 4

A comparative mixed solution 4 was obtained in the same manner as in Example 1, except that an aconitic acid was used instead of the oxalic acid in Example 1.
<Stability Test 14>
A sunny greenhouse comparative petri dish 4 and a dark place comparative petri dish 4 were obtained to conduct the stability test in the same manner as in the stability test 1, except that the comparative mixed solution 4 was used instead of the mixed solution 1.

As a result, the residual ratio of the compound X in the sunny greenhouse comparative petri dish 4 was approximately 0.3 fold of the sunny greenhouse comparative petri dish 1. The residual ratio of the compound X in the dark place comparative petri dish 4 was approximately 0.6 fold of the dark place comparative petri dish 1.

It was confirmed from the above-results that the presence of the aconitic acid contributed to the promotion of the photolysis and hydrolysis of the compound X.

Comparative Example 5

A comparative mixed solution 5 was obtained in the same manner as in Example 1, except that a succinic acid was used instead of the oxalic acid in Example 1.
<Stability Test 16>
A sunny greenhouse comparative petri dish 5 and a dark place comparative petri dish 5 were obtained to conduct the stability test in the same manner as in the stability test 1, except that the comparative mixed solution 5 was used instead of the mixed solution 1.

As a result, the residual ratio of the compound X in the sunny greenhouse comparative petri dish 5 was approximately 0.6 fold of the sunny greenhouse comparative petri dish 1. The residual ratio of the compound X in the dark place comparative petri dish 5 was approximately 0.6 fold of the dark place comparative petri dish 1.

It was confirmed from the above-results that the presence of the succinic acid contributed to the promotion of the photolysis and hydrolysis of the compound X.

Comparative Example 6

A comparative mixed solution 6 was obtained in the same manner as in Example 1, except that a terephthalic acid was used instead of the oxalic acid in Example 1.
<Stability Test 16>
A dark place comparative petri dish 6 was obtained to conduct the stability test in the same manner as in the stability test 1, except that the comparative mixed solution 6 was used instead of the mixed solution 1.

As a result, the residual ratio of the compound X in the dark place comparative petri dish 6 was approximately 0.6 fold of the dark place comparative petri dish 1.

It was confirmed from the above-results that the presence of the terephthalic acid contributed to the promotion of the hydrolysis of the compound X.

Comparative Example 7

A comparative mixed solution 7 was obtained in the same manner as in Example 1, except that an adipic acid was used instead of the oxalic acid in Example 1.
<Stability Test 17>
A sunny greenhouse comparative petri dish 7 and a dark place comparative petri dish 7 were obtained to conduct the stability test in the same manner as in the stability test 1, except that the comparative mixed solution 7 was used instead of the mixed solution 1.

As a result, the residual ratio of the compound X in the sunny greenhouse comparative petri dish 7 was approximately 0.7 fold of the sunny greenhouse comparative petri dish 1. The residual ratio of the compound X in the dark place comparative petri dish 7 was approximately 0.5 fold of the dark place comparative petri dish 1.

It was confirmed from the above-results that the presence of the adipic acid contributed to the promotion of the photolysis and hydrolysis of the compound X.

Comparative Example 8

A comparative mixed solution 8 was obtained in the same manner as in Example 1, except that a malonic acid was used instead of the oxalic acid in Example 1.
<Stability Test 18>
A dark place comparative petri dish 8 was obtained to conduct the stability test in the same manner as in the stability test 1, except that the comparative mixed solution 8 was used instead of the mixed solution 1.

As a result, the residual ratio of the compound X in the dark place comparative petri dish 8 was approximately 0.5 fold of the dark place comparative petri dish 1.

It was confirmed from the above-results that the presence of the malonic acid contributed to the promotion of the hydrolysis of the compound X.

Comparative Example 9

A comparative mixed solution 9 was obtained in the same manner as in Example 1, except that an acrylic acid was used instead of the oxalic acid in Example 1.
<Stability Test 19>
A sunny greenhouse comparative petri dish 9 and a dark place comparative petri dish 9 were obtained to conduct the stability test in the same manner as in the stability test 1, except that the comparative mixed solution 9 was used instead of the mixed solution 1.

As a result, the residual ratio of the compound X in the sunny greenhouse comparative petri dish 9 was approximately 0.6 fold of the sunny greenhouse comparative petri dish 1. The residual ratio of the compound X in the dark place comparative petri dish 9 was approximately 0.3 fold of the dark place comparative petri dish 1.

It was confirmed from the above-results that the presence of the acrylic acid contributed to the promotion of the photolysis and hydrolysis of the compound X.

Comparative Example 10

A comparative mixed solution 10 was obtained in the same manner as in Example 1, except that a phthalic acid was used instead of the oxalic acid in Example 1.
<Stability Test 20>
A sunny greenhouse comparative petri dish 10 and a dark place comparative petri dish 10 were obtained to conduct the stability test in the same manner as in the stability test 1, except that the comparative mixed solution 10 was used instead of the mixed solution 1.

As a result, the compound X was not detected in the sunny greenhouse comparative petri dish 10 and the dark place comparative petri dish 10, and it was confirmed that the compound X is absent therein.

It was confirmed from the above-results that the presence of the phthalic acid contributed to the promotion of the photolysis and hydrolysis of the compound X.

Example 12

20.2 parts of the compound X, 2.5 parts of a POE tristyrylphenyl ether, 0.5 parts of a POE/POP block copolymer, 5 parts of a propylene glycol, 0.5 parts of an antifoam, 0.3 parts of a preservative, and 21.4 parts of water were mixed well.

The mixture was wet-milled using a bead mill (DYNO-MILL RESEARCH LAB: manufactured by Shinmaru Enterprises Corporation) using zircon beads.

19.7 parts of 1% xanthan gum aqueous solution, 9.9 parts of 5% bentonite aqueous suspension, and 20 parts of trimethylolpropane (that is the additive disclosed in Example 6) were added to the pulverized product, and mixed well to obtain a uniform aqueous suspension state agrochemical composition (formulation 1).

(Stability Test)

The formulation was diluted with water at 2000 fold, and then sprayed onto apples. 5 apple leaves were collected immediately after spraying, or 4 days, 7 days, or 14 days after spraying, the front surface and the back surface thereof were washed with 10 ml of acetonitrile, and then 40 μl of the washing liquid was subjected to HPLC. The peak area attributable to the compound X was measured. The areas of the apple leaves after being washed were measured using a planimeter (automatic planimeter AAM-8 type: manufactured by Hayashi Denko co., ltd.). The peak area was converted to the peak area per 1 cm$^2$ of the leaf. The peak area per 1 cm$^2$ of the leaf immediately after spraying was determined as 100%, and the ratio of the peak area per 1 cm$^2$ of the leaf 4 days, 7 days, or 14 days after spraying, relative to the peak are per 1 cm$^2$ of the leaf immediately after spraying, was calculated as the residual ratio of the compound X (%).

The results of the stability test are shown in Table 1. Even 14 days after spraying, approximately 90% of the compound X remained.

Example 13

20.2 parts of the compound X, 2.5 parts of a POE tristyrylphenyl ether, 0.5 parts of a POE/POP block copolymer, 5 parts of a propylene glycol, 0.5 parts of an antifoam, 0.3 parts of a preservative, and 36 parts of water were mixed well.

The mixture was wet-milled using a bead mill (DYNO-MILL RESEARCH LAB: manufactured by Shinmaru Enterprises Corporation) using zircon beads.

20 parts of 1% xanthan gum aqueous solution, 10 parts of 5% bentonite aqueous suspension, and 5 parts of a sodium salt of maleic acid-2,4,4-trimethylpentene copolymer were added to the pulverized product, and mixed well to obtain a uniform aqueous suspension state agrochemical composition (formulation 2).

The stability test was conducted in the same way as that of Example 12. The results are shown in Table 1. Approximately 64% of the compound X remained even 14 days after spraying.

Example 14

20.2 parts of the compound X, 2.5 parts of a POE tristyrylphenyl ether, 0.5 parts of a POE/POP block copolymer, 5 parts of a propylene glycol, 0.5 parts of an antifoam, 0.3 parts of a preservative, and 21.4 parts of water were mixed well.

The mixture was wet-milled using a bead mill (DYNO-MILL RESEARCH LAB: manufactured by Shinmaru Enterprises Corporation) using zircon beads.

16.4 parts of 1% xanthan gum aqueous solution, 8.2 parts of 5% bentonite aqueous suspension, 20 parts of trimethylolpropane, and 5 parts of a sodium salt of maleic acid-2,4,4-trimethylpentene copolymer were added to the pulverized product, and mixed well to obtain a uniform aqueous suspension state agrochemical composition (formulation 3).

The stability test was conducted in the same way as that of Example 13. The results are shown in Table 1. Approximately 74% of the compound X remained even 14 days after spraying.

Comparative Example 11

20.2 parts of the compound X, 2.5 parts of a POE tristyrylphenyl ether, 0.5 parts of a POE/POP block copolymer, 5 parts of a propylene glycol, 0.5 parts of an antifoam, 0.3 parts of a preservative, and 41 parts of water were mixed well.

The mixture was wet-milled using a bead mill (DYNO-MILL RESEARCH LAB: manufactured by Shinmaru Enterprises Corporation) using zircon beads.

20 parts of 1% xanthan gum aqueous solution and 10 parts of 5% bentonite aqueous suspension were added to the pulverized product, and mixed well to obtain a uniform aqueous suspension state agrochemical composition (formulation 4).

The stability test was conducted in the same way as that of Example 13. The results are shown in Table 1. Approximately 52% of the compound X was reduced 14 days after spraying.

TABLE 1

| | Peak area per 1 cm$^2$ of leaf | | | | Residual ratio (%) | | | |
|---|---|---|---|---|---|---|---|---|
| | Immediately after spraying | 4 days after spraying | 7 days after spraying | 14 days after spraying | Immediately after spraying | 4 days after spraying | 7 days after spraying | 14 days after spraying |
| Formulation 1 | 7399 | 7191 | 5582 | 6655 | 100 | 97.2 | 75.4 | 89.9 |
| Formulation 2 | 6929 | 6731 | 6131 | 4443 | 100 | 97.1 | 88.5 | 64.1 |
| Formulation 3 | 6393 | 6532 | 5456 | 4732 | 100 | 102.2 | 85.3 | 74.0 |
| Formulation 4 | 7477 | 6007 | 4750 | 3613 | 100 | 80.3 | 63.5 | 48.3 |

It was confirmed from the comparison of the results of the formulations 1 and 3 with that of the formulation 4 that the presence of the trimethylolpropane contributed to the improvement of the stability of the compound X.

In addition, it was confirmed from the comparison of the results of the formulations 2 and 3 with that of the formulation 4 that the presence of the polycarboxylic acid contributed to the improvement of the stability of the compound X.

It is particularly confirmed from the result of the formulation 3 that effects of suppressing initial degradation of the compound X are largely exhibited with the coexistence of the trimethylolpropane and the polycarboxylic acid.

INDUSTRIAL APPLICABILITY

The agrochemical composition according to the present invention realizes a high residual ratio of a compound having an azabicyclo structure as an agrochemical active ingredient after being sprayed. The use of the agrochemical composition according to the present invention makes is possible to exhibit acaricidal effect over a long-term period to control mites harmful to agricultural crops.

The invention claimed is:

1. An agrochemical composition comprising: a component (A): a compound represented by formula (X) or a salt thereof;

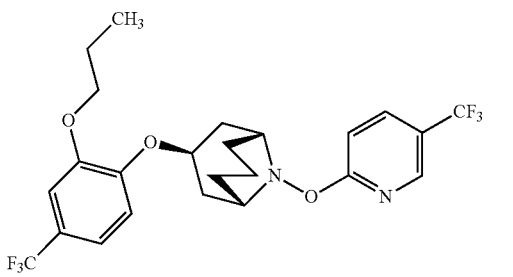
(X)

a component (B): a hydrolysis inhibitor which is at least one selected from the group consisting of trimethoylpropane, a oxalic acid, a gallic acid, a tartaric acid, a starch, a cellulose, and sorbitol; wherein the agrochemical composition further comprises a surfactant in an amount of 0 to 5% by mass relative to the total mass of the composition; and wherein the hydrolysis inhibitor is present in an amount that increases the amount of the compound Formula (X) 24 hours after the compound, an ascorbic acid, and the hydrolysis inhibitor are mixed and then left in a dark place or under the sunshine, in comparison with the case where no hydrolysis inhibitor is added.

2. The agrochemical composition according to claim 1, wherein the component (B) is trimethoylpropane.

3. The agrochemical composition according to claim 1, wherein the component (B) is at least one selected from the group consisting of an oxalic acid, a gallic acid, a tartaric acid, a starch, a cellulose, and sorbitol.

4. The agrochemical composition according to claim 2, further comprising a component (C): a polycarboxylic acid that is an alkali metal salt of a copolymer of a maleic acid and an alkene.

5. The agrochemical composition according to claim 2, wherein, relative to a total mass of the agrochemical composition, an amount of the component (A) is 1 to 50% by mass, an amount of the component (B) is 1 to 40% by mass, and a mass ratio of the component (A)/the component (B) is 20/1 to 1/20.

6. An agrochemical composition according to claim 1, wherein the agrochemical composition is in an aqueous suspension state.

7. The agrochemical composition according to claim 3, wherein, relative to a total mass of the agrochemical composition, an amount of the component (A) is 1 to 50% by mass, an amount of the component (B) is 1 to 40% by mass, and a mass ratio of the component (A)/the component (B) is 20/1 to 1/20.

8. The agrochemical composition according to claim 1, wherein an amount of the component (A) contained in the agrochemical composition is 10 to 25% by mass relative to the total mass of the composition.

9. The agrochemical composition according to claim 1, wherein an amount of the surfactant is 0.05 to 5% by mass relative to the total mass of the composition.

10. The agrochemical composition according to claim 1, wherein the composition further comprises an antifoam compound in an amount of 0.1 to 5% by mass relative to the total mass of the composition.

11. The agrochemical composition according to claim 1, wherein the agrochemical composition is an emulsifiable concentrate.

12. The agrochemical composition according to claim 1, wherein the agrochemical composition is a wettable powder.

13. The agrochemical composition according to claim 1, wherein a mass ratio of the component (A)/the component (B) in the agrochemical composition is 1/10 to 10/1.

14. The agrochemical composition according to claim 4, wherein component (C) is a sodium salt of a maleic acid-2,2,4-trimethylpentene copolymer.

* * * * *